(12) United States Patent
Abazid et al.

(10) Patent No.: US 11,823,546 B1
(45) Date of Patent: Nov. 21, 2023

(54) BREASTFEEDING DEVICE TO PREVENT BABY SUFFOCATION

(71) Applicant: KING FAISAL UNIVERSITY, Al-Ahsa (SA)

(72) Inventors: Mohammad Alakel Abazid, Al-Ahsa (SA); Hanan Abdullah, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/166,469

(22) Filed: Feb. 8, 2023

(51) Int. Cl.
G08B 21/02 (2006.01)
A61B 5/00 (2006.01)
A61M 1/06 (2006.01)

(52) U.S. Cl.
CPC ............ *G08B 21/0211* (2013.01); *A61B 5/00* (2013.01); *G08B 21/0277* (2013.01); *A61M 1/06* (2013.01)

(58) Field of Classification Search
CPC ......... A61B 5/00; A61B 5/0022; A61B 5/053; A61B 5/06; A61B 5/107; A61B 5/4312; A61B 5/48; A61B 5/6814; A61B 5/6823; A61J 9/00; B65D 83/00; B65D 85/72; G08B 21/02; G08B 21/20205; G08B 21/0206; G08B 21/0211; G08B 21/0277; A61M 1/06
See application file for complete search history.

(56) References Cited

U.S. PATENT DOCUMENTS

| | | | |
|---|---|---|---|
| 6,237,599 B1 | 5/2001 | Maulding et al. | |
| 2005/0011008 A1 | 1/2005 | Welch et al. | |
| 2011/0087078 A1* | 4/2011 | Zemel | A61B 5/4312 600/300 |
| 2016/0287481 A1* | 10/2016 | Chin | G16H 20/10 |
| 2017/0172485 A1* | 6/2017 | Makower | A61B 5/4312 |
| 2017/0266400 A1* | 9/2017 | McCarthy | A61M 16/06 |
| 2019/0374438 A1* | 12/2019 | Dellimore | A61J 13/00 |
| 2020/0121241 A1* | 4/2020 | Hafezi | A61B 5/7475 |

FOREIGN PATENT DOCUMENTS

| | | |
|---|---|---|
| CA | 2328673 A1 | 7/2001 |
| IN | 202041009023 A1 | 3/2020 |
| KR | 1020170083925 A1 | 1/2016 |

OTHER PUBLICATIONS

NPL Search (Apr. 12, 2023).*

* cited by examiner

*Primary Examiner* — Van T Trieu
(74) *Attorney, Agent, or Firm* — Nath, Goldberg & Meyer; Richard C. Litman

(57) ABSTRACT

The breastfeeding device to prevent baby suffocation includes a main unit and a remote unit. The main unit is mounted on a silicon pad or patch having an adhesive layer for attaching the main unit to one of the mother's breasts. The main unit includes a microcontroller having a sensor, such as a pressure sensor, connected thereto, either directly on the same printed circuit board or mounted external to the main unit and connected to the microcontroller by a wire or cable. The main unit has a transmitter mounted thereon for sending a signal to the remote unit when the sensor detects too much pressure being applied to the baby's mouth and nose. The remote unit has a receiver for receiving the signal, and a microcontroller for switching on an audible alarm when such a signal is received.

17 Claims, 2 Drawing Sheets

BREASTFEEDING DEVICE TO PREVENT BABY SUFFOCATION

BACKGROUND

1. Field

The disclosure of the present patent application relates to infant care accessories, and particularly to a breastfeeding device to prevent baby suffocation.

2. Description of the Related Art

According to the U.S. Center for Disease Control (CDC), breastfed babies, on average, need to be fed every two to four hours. Obviously, such a schedule may place a great strain on the mother, who may not be able to obtain sufficient rest or sleep. While expressing breast milk by hand or breast pump and storing the breast milk in bottles in a refrigerator may offer a partial solution, it is not always a viable option and is often regarded as not being as satisfactory as feeding the baby directly from the mother's breast. There are some reports in the literature of incidents where the mother has fallen asleep while breastfeeding her infant, with the result of a phenomenon known as "breast overlay" in which the infant's nose and mouth have been covered under one of the mother's breasts, causing infant suffocation and death. The extent to which this may be a problem is difficult to quantify, since such accidental deaths have frequently been reported as due to sudden infant death syndrome (SIDS). However, there is no doubt that when accidental death of an infant occurs due to the breast overlay phenomenon, it represents a great personal tragedy and may result in great strain on the marital relationship, with resulting costs to society. There is a need for a warning system that would sound an alert or alarm to waken the mother when she falls asleep during breastfeeding to prevent such accidental deaths from occurring. Thus, a breastfeeding device to prevent baby suffocation solving the aforementioned problems is desired.

SUMMARY

The breastfeeding device to prevent baby suffocation includes a main unit and a remote unit. The main unit is mounted on a silicon pad or patch having an adhesive layer for attaching the main unit to one of the mother's breasts. The main unit includes a microcontroller having a sensor, such as a pressure sensor, connected thereto, either directly on the same printed circuit board or mounted external to the main unit and connected to the microcontroller by a wire or cable. The main unit may have an analog-to-digital converter connected between the sensor and the microcontroller. The main unit has a transmitter mounted thereon for sending a signal to the remote unit when the sensor detects too much pressure being applied to the baby's mouth and nose. The remote unit has a receiver for receiving the signal, and a microcontroller for switching on an audible alarm when such a signal is received. The remote unit may be placed on a nightstand adjacent the mother, or any other convenient location.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The breastfeeding device to prevent baby suffocation includes a main unit and a remote unit. The main unit is mounted on a silicon pad or patch having an adhesive layer for attaching the main unit to one of the mother's breasts. The main unit includes a microcontroller having a sensor, such as a pressure sensor, connected thereto, either directly on the same printed circuit board or mounted external to the main unit and connected to the microcontroller by a wire or cable. The main unit may have an analog-to-digital converter connected between the sensor and the microcontroller. The main unit has a transmitter mounted thereon for sending a signal to the remote unit when the sensor detects too much pressure being applied to the baby's mouth and nose. The remote unit has a receiver for receiving the signal, and a microcontroller for switching on an audible alarm when such a signal is received. The remote unit may be placed on a nightstand adjacent the mother, or any other convenient location.

Figure 1:
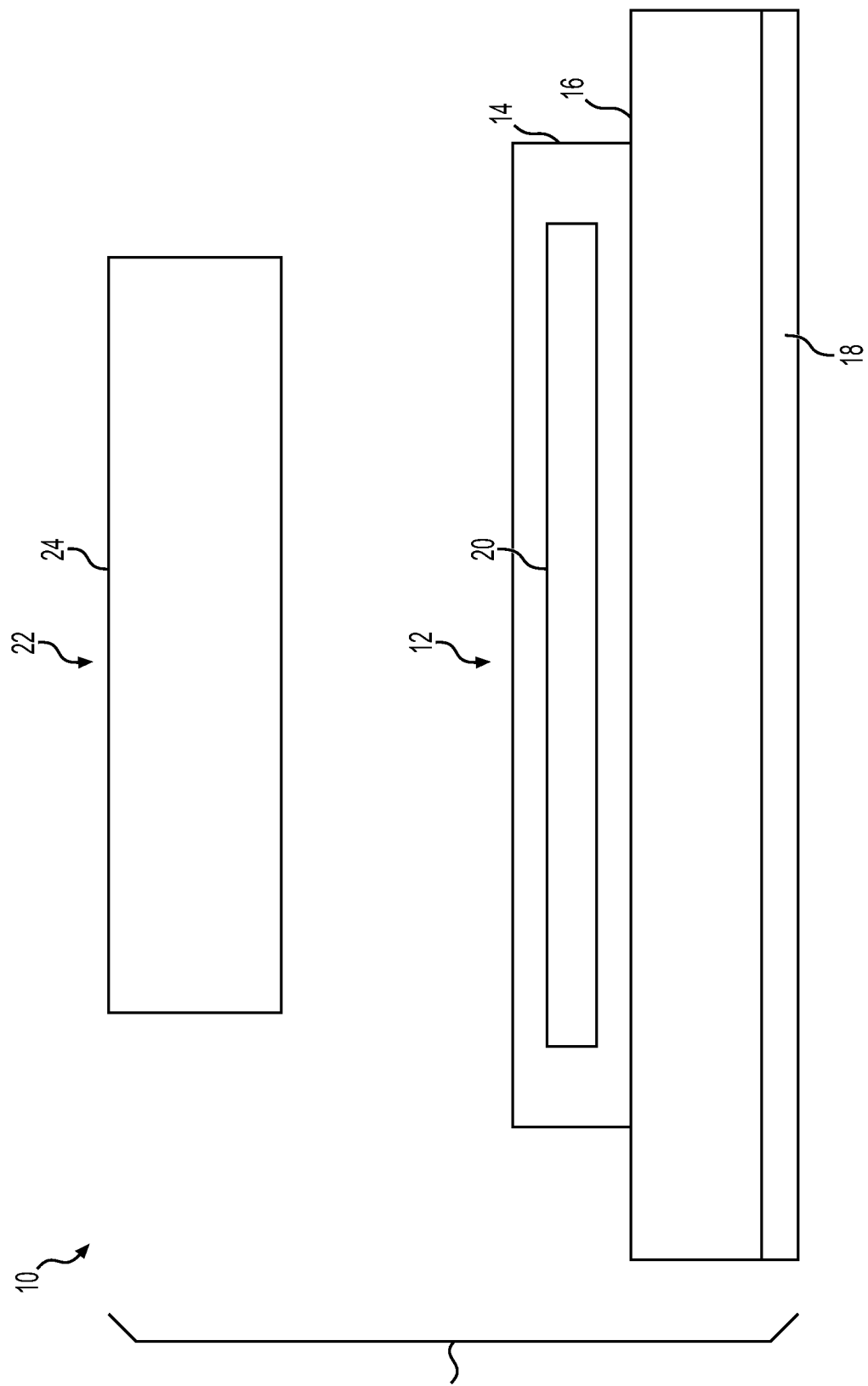
FIG. 1 is a side view of a breastfeeding device to prevent baby suffocation, largely schematic.

As shown in FIG. 1, the breastfeeding device to prevent baby suffocation, designated generally as 10 in the drawings, includes a main unit 12 housed in a case or compartment 14 mounted on a silicon pad or patch 16. The bottom surface of the silicon pad 16 has an adhesive layer 18 of biocompatible adhesive coated thereon or attached thereto. The adhesive layer 18 is adapted for attaching the main unit 12 to one of the mother's breasts, on or under the breast. The main unit 12 includes a sensor 20, which may be mounted on a circuit board containing the other components of the main unit 12 and bear against or extend through at least one side or face of the case or compartment 14 housing the main unit 12. Although shown in the drawings as being mounted on the main unit, it will be understood that in an alternative embodiment, the sensor 20 may be disposed external to the case or compartment 14 housing the main unit 12 and be electrically connected to the main unit 12 by a wire or cable. The breastfeeding device 10 also includes a remote unit 22, which may be mounted in a case or container 24 having any desired dimensions or configuration. In use, the remote unit 22 may be placed on a nightstand or other article of furniture adjacent the location where the mother will be during breastfeeding, or may have a lanyard for attachment to the mother's neck or limbs.

Figure 2:
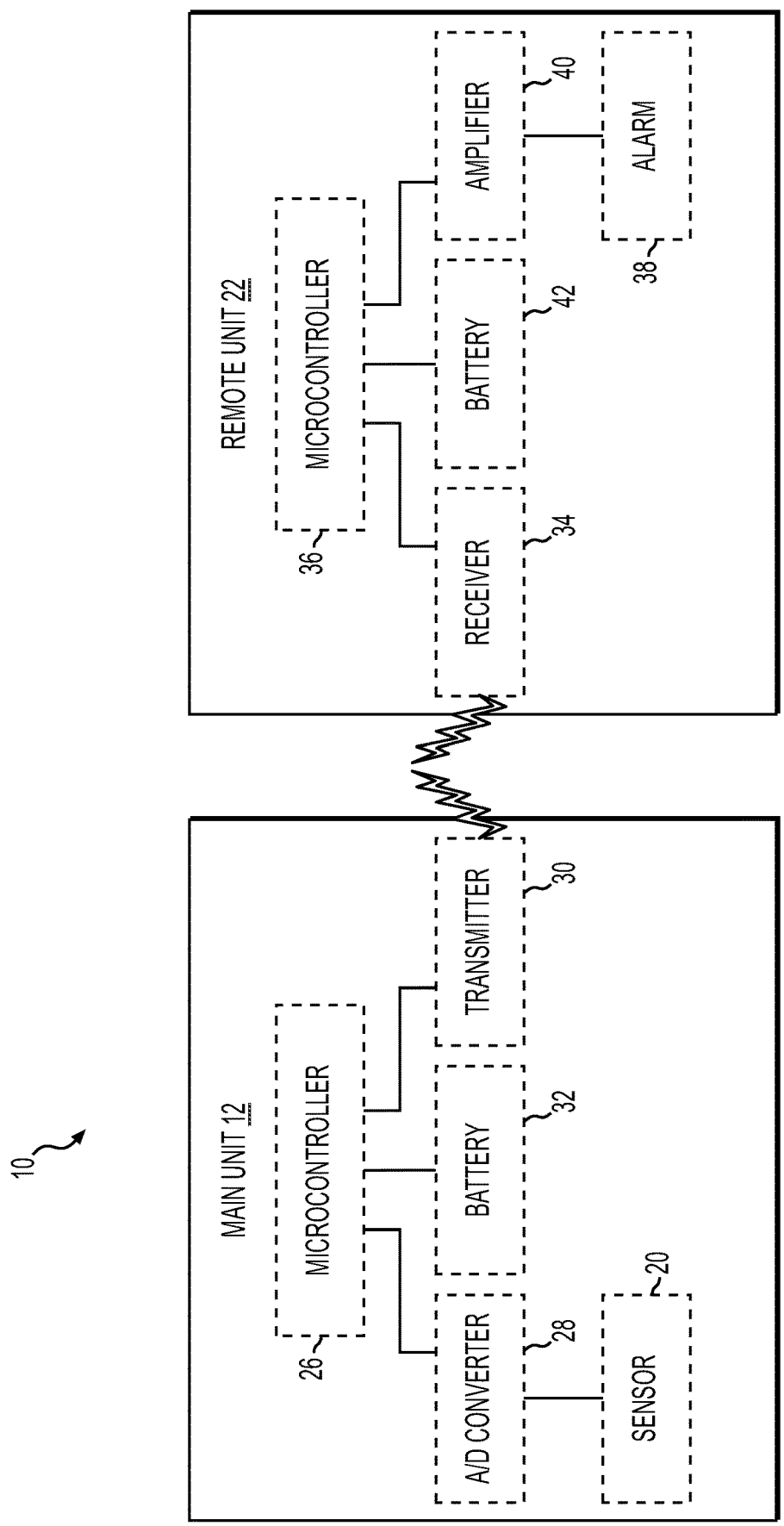
FIG. 2 is a block diagram of a breastfeeding device to prevent baby suffocation, showing the components of the main unit and the remote unit.

As shown in FIG. 2, the main unit 12 has a sensor 20 configured for detecting when the mother's breast is applying enough pressure to the baby's nose or mouth to risk suffocation of the baby. The sensor 20 may be a pressure sensor, a force-sensitive resistor, or in some embodiments, a proximity sensor, all of which are well known in the art and need not be described further. The sensor 20 may be mounted on the same printed circuit board as the main unit's microcontroller 26 inside the main unit's case or compartment 14, or may be mounted on the silicon pad 16 external to the case or compartment 14 and electrically connected to the microcontroller 26 by wires or cable. The sensor 20 may emit either an analog signal proportional to the pressure applied to the sensor 20, or may emit a digital signal corresponding to the pressure applied to the sensor 20. In case the main unit's microcontroller 26 does not have analog terminals or circuitry configured for receiving analog signals, the main unit 12 may have an analog-to-digital converter 28 for converting the sensor's analog output into a digital signal for input to the microcontroller 26.

The main unit 12 has a transmitter (or transceiver) 30 configured for sending a wireless alert or alarm signal to the remote unit 22 when the pressure signal from the sensor 20 exceeds a predetermined limit. The transmitter 30 may transmit the alert or alarm signal by Bluetooth protocol, by WiFi signal, or by RF transmission, depending on range requirements. The main unit 12, including the microcontroller 26, the A/D converter, the sensor 20, and the transmitter 30, may be powered by a battery 32.

The remote unit 22 has a corresponding receiver (or transceiver) 34 for receiving the alert or alarm signal from the main unit 12. The remote unit 22 also has a microcontroller 36 that receives the alert or alarm signal from the receiver 34. In response to receiving the alert or alarm signal from the main unit 12, the remote unit's microcontroller 36 outputs a command to an alarm transducer 38, which may emit any type of audible alarm, such as a buzzer, a ball, or a recorded voice message played by a voice synthesizer or other recording device for alerting the breastfeeding mother (or a companion) to the potential danger to the infant. If needed, the remote unit's microcontroller 36 may output a drive signal to the alarm transducer 38 through an amplifier 40 to increase the volume of the audible signal emitted by the alarm transducer 38. All components in the remote unit 22 may also be powered by a battery 42.

Thus, the breastfeeding device to prevent baby suffocation provides a means for detecting the danger of infant suffocation if the mother falls asleep during breastfeeding and generates an audible alarm signal to alert the mother to the impending danger to her child.

It is to be understood that the breastfeeding device to prevent baby suffocation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A breastfeeding device to prevent baby suffocation, comprising:
   a main unit adapted for attachment to a mother's breast, the main unit having:
      a sensor configured for measuring pressure applied to a baby's nose and mouth when the mother falls asleep while breastfeeding the baby, wherein said measured pressure provides an indication of a restricted respiratory air flow while the baby is breastfeeding; and
      a transmitter connected to the sensor, the transmitter being configured for transmitting a wireless request for an alarm when the measured pressure reaches or exceeds a predetermined limit; and
   a remote unit adapted for placement within hearing distance of the mother, the remote unit having:
      a receiver configured for receiving the wireless request for an alarm from the transmitter of the main unit; and
      an alarm transducer connected to the receiver, the alarm transducer being configured for emitting an audible alarm signal to alert the mother of a risk of suffocation of the baby due to said restricted respiratory air flow while the baby is breastfeeding.

2. The breastfeeding device according to claim 1, said main unit further comprises a silicon pad having a bottom surface and a layer of biocompatible adhesive coated on the bottom surface for attaching the silicon pad to the mother's breast, the silicon pad having a case mounted thereon for housing at least some main unit components.

3. The breastfeeding device according to claim 1, wherein said transmitter and said receiver communicate with each other by Bluetooth protocol.

4. The breastfeeding device according to claim 1, wherein said transmitter and said receiver communicate with each other by WiFi protocol.

5. The breastfeeding device according to claim 1, wherein said transmitter and said receiver communicate with each other by radio frequency (RF) protocol.

6. The breastfeeding device according to claim 1, wherein said sensor comprises a pressure sensor.

7. The breastfeeding device according to claim 1, wherein said sensor comprises a pressure-sensitive resistor.

8. The breastfeeding device according to claim 1, wherein said sensor comprises a proximity sensor.

9. The breastfeeding device according to claim 1, wherein said main unit further comprises a main unit microcontroller connected between said sensor and said transmitter, the main unit microcontroller being configured for determining when said sensor's measurements reach or exceed the predetermine limit and signaling said transmitter to request an alarm from said remote unit in response thereto.

10. The breastfeeding device according to claim 9, wherein said sensor outputs an analog signal corresponding to measurements made by said sensor.

11. The breastfeeding device according to claim 10, wherein said main unit further comprises an analog-to-digital converter connected between said sensor and said main unit microcontroller, the analog-to-digital converter being configured for converting the analog output signal of said sensor to a corresponding digital input signal to said main unit microcontroller.

12. The breastfeeding device according to claim 1, wherein said alarm transducer is a bell.

13. The breastfeeding device according to claim 1, wherein said alarm transducer is a buzzer.

14. The breastfeeding device according to claim 1, wherein said alarm transducer is a voice synthesizer configured to play a pre-recorded voice message.

15. The breastfeeding device according to claim 1, wherein said remote unit further comprises a remote unit microcontroller connected between the receiver and the alarm transducer, the remote unit microcontroller being configured to output a signal commanding the alarm transducer to emit an audible alarm in response to an input signal from the receiver of a request for an alarm received from said main unit.

16. The breastfeeding device according to claim 1, wherein said remote unit further comprises an amplifier connected between said remote unit microcontroller and said alarm transducer.

17. The breastfeeding device according to claim 1, wherein said main unit and said remote unit each further comprise a battery, said main unit and said remote unit each being battery powered, respectively.

* * * * *